United States Patent [19]

Stevens et al.

[11] Patent Number: 4,894,227

[45] Date of Patent: * Jan. 16, 1990

[54] COMPOSITION OF IMMUNOTOXINS WITH INTERLEUKIN-2

[75] Inventors: Paul Stevens; L. L. Houston, both of Oakland; Kirston E. Koths, El Cerrito; Brian Issell, Moraga, all of Calif.

[73] Assignee: Cetus Corporation, Emeryville, Calif.

[*] Notice: The portion of the term of this patent subsequent to Sep. 5, 2006 has been disclaimed.

[21] Appl. No.: 55,681

[22] Filed: May 29, 1987

Related U.S. Application Data

[63] Continuation-in-part of Ser. No. 892,596, Aug. 1, 1986.

[51] Int. Cl.[4] .............................................. A61K 37/02
[52] U.S. Cl. ................................ 424/85.2; 424/85.1; 424/85.8; 424/85.91; 514/2; 514/8; 514/21; 514/885; 530/351; 530/389; 530/391
[58] Field of Search ...................... 424/85, 85.1, 85.2, 424/85.8, 85.91; 514/2, 8, 21, 885; 530/351, 389, 391

[56] References Cited

U.S. PATENT DOCUMENTS

4,604,377 8/1986 Fernandes et al. .................. 435/68
4,676,980 9/1987 Segal et al. .......................... 424/85

FOREIGN PATENT DOCUMENTS

0153114 8/1985 European Pat. Off. .
0189849 8/1986 European Pat. Off. .
0220858 5/1987 European Pat. Off. .
85/04328 10/1985 PCT Int'l Appl. .
87/00054 1/1987 PCT Int'l Appl. .

OTHER PUBLICATIONS

Nomi et al., Cancer Res., 46, 1986, pp. 5606-5610.
Lee et al., Neural Clin, 3(4), 1985, pp. 901-917 (abstract).
Kosugi et al., Gan to Kayaku Ryoho, 11(8), 1984, pp. 1527-1535 (abstract).
Dr. Rosenstein et al., J. Immunol. (1986), 137:1735-1742.
Shaw et al., Cell Immunol., (1985), 91:193-200.
Shaw et al., Cell. Immunol., (1985), 90:547-554.
Nomomura et al., Hepatology, (1984), 4:1087.
Kimber et al., J. Clin. Lab. Immunol., (1984), 15:77-84.
Lotze et al., J. Immunol., (1985), 135:2865.
Alan Houghton, Sloan Kettering Cancer Institute, Protocol Activation Form (Clinical Trial) (1985).
SCRIP No. 1213, p. 30, (Jun. 12, 1987).
Honsik et al., Proc. Nat. Acad. Sci. (U.S.A.) 83:7893-7897, (1986).
Philip et al., Nature, 323: 86-89 (1986).
Perez et al., J. Immunol., 137: 2069-2072, (1986).
Perez et al., J. Exp. Med., 163: 166-178, (1986).

Primary Examiner—Howard E. Schain
Assistant Examiner—Garnette D. Draper
Attorney, Agent, or Firm—Gregory J. Giotta; Janet E. Hasak; Albert P. Halluin

[57] ABSTRACT

Anti-tumor activity in humans can be augmented by administering to the mammalian host a pharmacologically effective amount of mammalian IL-2 and at least one immunotoxin that binds selectively to human tumor cells. The IL-2 and immunotoxin are preferably administered separately to the host. The composition is useful for prophylactic or therapeutic treatment of such cancers as ovarian and breast cancer.

10 Claims, No Drawings

COMPOSITION OF IMMUNOTOXINS WITH INTERLEUKIN-2

This application is a continuation-in-part application of copending U.S. Ser. No. 892,596 filed Aug. 1, 1986.

BACKGROUND OF THE INVENTION

1. Field of the Invention

This invention relates to use of a combination of interleukin-2 and an immunotoxin directed against tumor cells in the therapeutic or prophylactic antitumor treatment of mammals using simultaneous or alternate administration of these components.

2. Background Art

Interleukin-2 (IL-2), a lymphokine produced by normal peripheral blood lymphocytes that induces proliferation of antigen or mitogen stimulated T cells after exposure to plant lectins, antigens, or other stimuli, was first described by Morgan, D. A., et al., *Science* (1976), 193:1007-1008. Then called T cell growth factor because of its ability to induce proliferation of stimulated T lymphocytes, now interleukin-2 is recognized as modulating a variety of functions of immune system cells in vitro and in vivo.

IL-2 was initially made by cultivating human peripheral blood lymphocytes (PBL) or other IL-2-producing cell lines. See, for example, U.S. Pat. No. 4,401,756 Recombinant DNA technology has provided an alternative to PBLs and cell lines for producing IL-2. Taniguchi, T. et al., *Nature* (1983), 302:305-310 and Devos, R., *Nucleic Acids Research* (1983), 11:4307-4323 have reported cloning the human IL-2 gene and expressing it in microorganisms.

U.S. Pat. No. 4,518,584 describes and claims muteins of IL-2 in which the cysteine normally occurring at position 125 of the wild-type or native molecule has been replaced with a neutral amino acid, such as serine or alanine Copending U.S. application Ser. No. 810,656 filed Dec. 17, 1985 discloses and claims an oxidation-resistant mutein such as IL-2 which is biologically active wherein a methionine residue of the parental protein which is susceptible to chloramine T or peroxide oxidation is replaced with a conservative amino acid such as alanine. The above IL-2 muteins possess the biological activity of native IL-2. U.S. Pat. Nos. 4,530,787 and 4,569,790 disclose and claim methods for purifying recombinant native IL-2 and muteins thereof, as well as the purified form of IL-2.

U.S. Pat. No. 4,604,377 issued Aug. 5, 1986 discloses an IL-2 composition suitable for reconstituting in a pharmaceutically acceptable aqueous vehicle composed of oxidized microbially produced recombinant IL-2. The IL-2 is noted as useful in combination with cytotoxic chemotherapy or irradiation or surgery in the treatment of malignant or pre-malignant diseases in a direct therapeutic or adjuvant setting or in combination with other immune-modulating drugs, lymphokines (e.g., IL-1, IL-3, CSF-1 and IFNs), or naturally occurring or inducible anti-cellular toxins.

Rosenberg and his coworkers have shown that systemic administration of recombinant IL-2 in high doses causes regression of established metastatic cancers in mice (Rosenberg et al., *J. Exp. Med.* (1985) 161:1169-1188); and, in conjunction with lymphokine-activated killer cells (Rosenberg, S. et al., *New Eng. J. Med.* (1985), 313:1485-1492), and tumor-infiltrating lymphocytes (Rosenberg et al., *Science* (1986) 233:1318-1321), in humans.

Since the mid-1970s, there have been numerous reports of murine monoclonal antibodies that interact with human breast cancer associated antigens. In these reported studies, mice were immunized and boosted with human milk fat globule proteins, breast cancer cell lines or breast cancer membrane extracts. Immune splenocytes were fused with mouse myeloma cells and hybridomas were selected based on some specificity of the culture supernatant for breast or breast cancer antigens. Taylor-Papadimitriou, J. et al., *Int. J. Cancer* (1981) 28:17-21; Yuan, D., et al., *JNCI* (1982) 68:719-728; Ciocca, D. R. et al., *Cancer Res.* (1982) 42:4256-4258.

More recently, investigators at Cetus Corporation have discovered murine monoclonal antibodies that bind selectively to human breast cancer cells, are IgGs or IgMs, and, when conjugated to ricin A chain to form an immunotoxin, exhibit a tissue culture inhibitory dose which results in 50% of control (untreated) protein synthesis (TCID 50%) at immunotoxin concentrations of less than about 10 nM against at least one of MCF-7, CAMA-1, SKBR-3, or BT-20 cells. These antibodies are described more fully in EPC Patent Publication No. 153,114 published Aug. 28, 1985, the disclosure of which is incorporated herein by reference.

In addition, researchers at Cetus Corporation have discovered murine monoclonal antibodies which do not bind to blood cells, have a breast tumor binding range of at least 0.25 (i.e., they bind to at least 25% of breast tumors tested) or have a breast cancer cell line binding range of greater than or equal to 0.25, have a normal tissue reactivity as defined below for human breast and/or ovarian cells equal to or less than 0.09, are IgGs or IgMs, and, when conjugated to an imaging moiety, produce a signal sufficient to image breast cancer tumors. These antibodies include most of those described above and are described more fully in European Pat. Pub. No. 220,858 published May 6, 1987, the disclosure of which is incorporated herein by reference.

Immunotoxins, which are comprised of an antibody conjugated to a toxin, have been used for therapy of various cancers to which the antibody is specific. Certain immunotoxin molecules may be too large to reach the tumor cells efficiently due to poor diffusion out of capillaries.

Combination chemotherapy using two or more anticancer drugs to treat malignant tumors in humans is currently in use in research and in the clinic. The anticancer drugs may be antimetabolites, alkylating agents, antibiotics, general poisons, etc. Combinations of drugs are administered in an attempt to obtain a synergistic cytotoxic effect on most cancers, e.g., carcinomas, melanomas, lymphomas and sarcomas, and to reduce or eliminate emergence of drug-resistant cells and to reduce side effects of each drug.

Dr. Rosenstein et al., *J. Immunol.* (1986) 137:1735-1742 disclosed that IL-2 increases the vascular permeability and rate of serum albumin diffusion into organs. Lotze et al., *J. Immunol.* (1985) 135:2865 disclosed that reversible fluid retention problems result from IL-2 administration.

To applicants' knowledge no one has administered immunotoxin and IL-2 to decrease or eliminate tumor burden

SUMMARY OF THE INVENTION

Accordingly, the present invention provides a composition suitable for parenteral or subcutaneous administration to a warm-blooded mammalian host for therapeutic or prophylactic treatment of tumor burden comprising a mixture, in pharmacologically effective amounts, of IL-2 from a mammalian species and at least one immunotoxin that binds selectively to cells containing the tumor burden.

In another aspect, the invention provides a method for therapeutic or prophylactic treatment of tumor burden in a warm-blooded mammalian host comprising administering to said host a pharmacologically effective amount of a combination of IL-2 from a mammalian species and at least one immunotoxin that binds selectively to cells containing the tumor burden.

Preferably the IL-2 is a recombinant human IL-2, and the monoclonal antibody employed in the immunotoxin selectively binds to human breast and/or ovarian cancer cells and has a G or M isotype, and the tumor burden line treated is breast and/or ovarian cancer.

The combination of IL-2 and immunotoxin(s) in pharmacologically effective amounts is expected to provide suitable treatment of a variety of forms of cancer, especially breast and ovarian cancers.

DESCRIPTION OF THE PREFERRED EMBODIMENTS

The term "therapeutic" treatment refers to administration to the mammalian host or patient of the IL-2 and immunotoxin(s) after the patient has developed cancer, (i.e., after a tumor burden has been determined), as measured by any means in the art, with resultant decrease or elimination of the existing tumor burden.

The term "propylactic" treatment refers to such administration to prevent recurrence of the cancer after therapeutic treatment has been administered.

The terms "cancer" and "tumor burden" refer to any neoplastic disorder, including such cellular disorders as, for example, renal cell cancer, Kaposi's sarcoma, chronic leukemia, breast cancer, sarcoma, prostate, pancreatic endometrial, and ovarian carcinomas, rectal cancer, throat cancer, melanoma, colon cancer, bladder cancer, mastocytoma, lung cancer and gastrointestinal or stomach cancer. In the method of the invention, the target tumor burden is advantageously breast and/or ovarian cancer.

The term "pharmacologically effective amount" refers to the total amount of each active component of the method or composition herein that is sufficient in showing a meaningful patient benefit, i.e., prolongation of life and/or reduction of disease. When the effective amounts defined herein are employed, more efficacy is obtained using the combination than using either component alone. As applied to an individual active ingredient administered alone, the term refers to that ingredient alone; when combinations are used, the term refers to combined amounts in the preparation that result in the therapeutic or prophylactic effect.

The term "recombinant" refers to IL-2 produced by recombinant DNA techniques wherein generally the gene coding for the IL-2 is cloned by known recombinant DNA technology. For example, the human IL-2 gene is inserted into a suitable DNA vector such as a bacterial plasmid, preferably an *E. coli* plasmid, to obtain a recombinant plasmid, and the plasmid is used to transform a suitable host. The gene is expressed in the host to produce the recombinant protein. Examples of suitable recombinant plasmids for this purpose include pBR322, pCR1, pMB9 and pSC1. The transformed host may be prokaryotic or eukaryotic, including mammalian, yeast, Aspergillus and insect cells. One preferred embodiment herein, but not the only preferred embodiment, employs bacterial cells as the host.

The term "pharmaceutically acceptable" refers to a carrier medium that does not interfere with the effectiveness of the biological activity of the active ingredients and that is not toxic to the hosts to which it is administered.

The term "immunotoxin" as used herein refers to a conjugate of an antibody or fragment of an antibody and a cytotoxic moiety. The antibody or fragment thereof employed must bind selectively to human tumor cells and be effective in an immunotoxin. The antibody is chosen from those described hereinafter if it is effective in the conjugated form. The cytotoxic moiety of the immunotoxin includes a cytotoxic drug or an enzymatically active toxin of bacterial or plant origin or an enzymatically active fragment ("A chain") of such a toxin. Examples of enzymatically active toxins and fragments thereof include diphtheria A chain, nonbinding fragments of diphtheria toxin, exotoxin A chain (from *Pseudomonas aeruoinosa*), ricin A chain, abrin A chain, modeccin A chain, alpha-sarcin, *Aleurites fordii* proteins, dianthin proteins, *Phytolacca americana* proteins (PAPI, PAPII, and PAP-S), momordica charantia inhibitor, curcin, crotin, saponaria officinalis inhibitor, gelonin, mitogellin, restrictocin, phenomycin, and enomycin. Ricin A chain, nonbinding active fragments of diphtheria toxin, abrin A chain, and PAPII are preferred. Most preferred is the ricin A chain.

As used herein, the term "selective binding to human tumor cells" refers to preferential binding of the antibodies of the immunotoxin to human cells that are cancerous or exhibit cancerous growth or other properties characteristic of cancer. The antibodies of the immunotoxins do not preferentially bind to normal healthy cells. Examples of such tumor cells include leukemia cells, prostrate cancer cells, colorectal cancer cells, breast cancer cells, ovarian cancer cells, rectal cancer cells, throat cancer cells, melanoma cells, colon cancer cells, bladder cancer cells, lung cancer cells, and gastrointestinal or stomach cancer cells. Most preferably, the antibodies of the immunotoxins selectively bind to breast and/or ovarian cancer cells, as opposed to binding to normal, non-cancerous cells.

As used herein with respect to the exemplified monoclonal anti-human breast cancer antibodies of the immunotoxins, the term "functional equivalent" means a monoclonal antibody that: (a) has a breast tumor binding range of at least 0.25 or has a breast cancer cell line range of greater than or equal to 0.25; (b) binds selectively to human breast cancer cells; (c) has a G or M isotype; and (d) binds to the same antigen or epitope as the exemplified monoclonal antibody, as determined by immunoprecipitation or crossblocking and sandwich immunoassay.

As described above, the term "functional equivalent" as used herein includes four criteria. The last of these criteria, binding to the same antigen or epitope as an exemplified monoclonal antibody, may be demonstrated by experiments which show crossblocking of an exemplified monoclonal antibody by the functionally equivalent monoclonal antibody. Crossblocking occurs as a result of an antibody binding to the same epitope on an antigen as that bound by one of the exemplified antibodies, or as a result of an antibody binding to a different epitope which is so closely situated on the same antigen that binding of an antibody to one epitope blocks the binding of an antibody to the second epitope. Crossblocking thus is one of the criteria by which one can determine that a functionally equivalent monoclonal antibody binds to the same antigen or epitope as an exemplified monoclonal antibody.

So-called "sandwich" assays are another method for determining whether an antibody of the immunotoxin binds the same antigen or epitope. In these assays, a first monoclonal antibody is bound to a support, for example, the surface of a microtitre plate well. After treatment to prevent nonspecific binding, a solubilized antigen preparation is added to the bound antibody. Subsequently, a second antibody, having a detectable label, for example, a chromogenic enzyme, is added. If the second antibody binds to the antigen, a different epitope specificity or multiple copies of the same epitope on the same antigen are indicated. If the second antibody fails to bind, either the same epitope specificity or different but proximal antigen specificity is indicated. The results of both the crossblocking and sandwich assay are further defined by a second series of tests such as immune precipitation or Western blotting to characterize the molecular weight(s) of the antigen(s) bound by both antibodies.

The American Type Culture Collection (ATCC), Rockville, Md. USA has a wide variety of cell lines on deposit which produce monoclonal antibodies to target tumors. For example, cell lines producing monoclonal antibodies to human non-small cell lung cancer include 703D4 (deposited as ATCC No. HB8301). Cell lines producing monoclonal antibodies to human melanoma cells include 704A1 (deposited as ATCC No. HB8302). Cell lines producing monoclonal antibodies to small cell carcinoma include the cell lines deposited as ATCC HB8462 and ATCC HB8711. Cell lines producing antibodies to pancreatic carcinoma of ductal origin include the hybridoma deposited as ATCC HB8504. A cell line producing antibodies which bind to an epitope present on adenocarcinomas of the stomach, colon, and pancreas, and to esophagus, breast and ovarian tumors, known as CSLEX1, is deposited as ATCC HB8580.

Conjugates of the antibody and cytotoxic moiety may be made using a variety of bifunctional protein modifying reagents. Examples of such reagents include N-succinimidyl-3-(2-pyridyldithio) propionate (SPDP), iminothiolane (IT), bifunctional derivatives of imidoesters such as dimethyl adipimidate·HCl, active esters such as disuccinimidyl suberate, aldehydes such as glutaraldehyde, bis-azido compounds such as bis (p-azidobenzoyl) hexanediamine, bis-diazonium derivatives such as bis-(p-diazonium-benzoyl)-ethylenediamine, diisocyanates such as tolylene-2,6-diisocyanate, and bis-active fluorine compounds such as 1,5-difluoro-2,4-dinitrobenzene.

The method of this invention involves administering to a warm-blooded mammalian host, including a mouse, rat, rabbit, primate, pig or human host, preferably a human patient, a pharmacologically effective amount of IL-2 and one or more immunotoxins that selectively bind to human tumor cells. The IL-2 and immunotoxin(s) may be combined in vitro before administration if neither is adversely affected chemically and both remain efficacious. Preferably, however, they are separately administered to the patient, in either order or simultaneously. An example is the protocol set forth in Examples 1 and 2 hereof, wherein the IL-2 and immunotoxin are administered separately.

The administration(s) may take place by any suitable technique, including parenteral administration. Examples of parenteral administration include intravenous, intraarterial, intramuscular, subcutaneous, and intraperitoneal, with intravenous, intramuscular and intraperitoneal administration being preferred.

As an example, the patient/host may be treated locally (as by peritumor or intramuscular injection) or systemically with a preparation having IL-2 activity until the capillaries begin to leak large proteins (about 6 days). Then the immunotoxin may be administered with or without the IL-2 for the prescribed duration of treatment. Alternatively, immunotoxin can be administered from day 1 of treatment. Local treatment with IL-2 to promote immunotoxin action may be followed with systemic (e.g., intraperitoneal or intravenous bolus) administration of IL-2 and immunotoxin.

The dose and dosage regimen will depend on whether the IL-2 and immunotoxin(s) are being administered separately or as a mixture, the type of immunotoxin(s) and cancer, the patient/host and the patient's history. The amount must be effective to achieve some tumor reduction or augmentation of LAK activity. The doses may be single doses or multiple doses. If multiple doses are employed, as preferred, the frequency of administration will depend, for example, on the type of component, cancer, dosage amounts, host, etc. For some types of cancers, daily administration may be effective, whereas for other types of cancer, administration every other day or every third day may be effective, but daily administration ineffective. The practitioner will be able to ascertain from clinical trials which route of administration and frequency of administration are most effective in humans in any particular case.

The dosage amount which appears to be most effective herein is one which results in regression in size of the tumor or complete disappearance or non-reappearance of the tumor, and is not toxic or is acceptably toxic to the host. Generally, such conditions as fever, chills and general malaise are considered acceptable. This optimum dose level will depend on many factors, for example, on the type of host and type of cancer, route, schedule and sequence of administration, existing tumor burden, the type of IL-2 and immunotoxin(s), and the definition of toxicity.

Toxicity to the host may be defined by the extent and type of side effects, with fever, chills and general malaise considered acceptable toxicity for the study herein, or sometimes by the amount of body weight gain or by death after a certain period of time. The reversible fluid retention in the body resulting from IL-2 administration is disclosed by Lotze, et al., *J. Immunol.*, 135:2865 (1985). If body weight gain is the criterion for toxicity, typically a gain of from 10 to 20% by weight will be tolerated, with greater than 20% gain being considered toxic.

If there is acceptable toxicity, and if there is pretreatment with recombinant, microbially produced IL-2 and/or concurrent administration daily for 14 days of the IL-2 and for 7 days of immunotoxin beginning at day 1 post-treatment, the dosage level of each administration of immunotoxin made with the anti-breast cancer antibody is 25 to 500 μg/kg of host weight of immunotoxin. The IL-2 level is that given above. If the host is immuno-compromised (i.e., nude mice, which have a genetic deficiency), the maximum tolerated dose may be lower.

In one preferred embodiment the IL-2 is given at the maximum tolerated dose daily for one week followed by giving one-half the maximum tolerated dose of IL-2 with concomitant administration of the maximum tolerated dose of immunotoxin.

For parenteral administration the IL-2 and immunotoxin(s) will generally each be formulated in a unit dosage injectable form (solution, suspension, emulsion), preferably in a pharmaceutically acceptable carrier medium that is inherently non-toxic and non-therapeutic. Examples of such vehicles include saline, Ringer's solution, dextrose solution, mannitol, and normal serum albumin. Nonaqueous vehicles such as fixed oils and ethyl oleate may also be used. The carrier medium may contain minor amounts of additives such as substances that enhance isotonicity, solubility, and/or chemical stability, e.g., buffers, detergents, and preservatives. The IL-2 and immunotoxin(s) will typically each be formulated in such carriers at a concentration of about 0.1 mg/ml to 100 mg/ml, preferably 0.2 to 1 mg/ml.

Alternatively, the IL-2 and immunotoxin(s) may be made into a sterile, stable lyophilized formulation in which the purified IL-2 and immunotoxin(s) are admixed with a water-soluble carrier such as mannitol, which provides bulk, and about 500 μg of a surfactant such as sodium dodecyl sulfate per mg of IL-2 or 0.01–0.05% in typical formulations to ensure the solubility of the recombinant IL-2 in water, if the immunotoxin is still active at such concentrations. The formulation is suitable for reconstitution in aqueous injections for parenteral administration and it is stable and well-tolerated in the mammalian host, particularly in human patients. The IL-2 formulation method is more completely described in U.S. Pat. No. 4,604,377 issued Aug. 5, 1986, the disclosure of which is incorporated herein by reference.

In an alternative IL-2 formulation, described in co-pending U.S. application Ser. No. 866,459, filed May 21, 1986, now abandoned, the disclosure of which is incorporated herein by reference, the IL-2 may be solubilized, not by a detergent, but by reacting the IL-2 with an activated polymer selected from polyethylene glycol homopolymers and polyoxyethylated polyols, said polymer having a molecular weight of from 300 to 100,000 daltons, preferably 350 to 40,000 daltons. The polymer is activated by conjugation with a coupling agent having terminal groups reactive with both the free amino or thiol groups of the IL-2 and the hydroxyl group of the polymer. Examples of such coupling agents include hydroxynitrobenzene sulfonic ester, cyanuric acid chloride, and N-hydroxysuccinimide. This modification eliminates the necessity of adding detergents to solubilize the IL-2 at physiological pH. The IL-2 is then formulated directly with the water-soluble carrier and buffer as described above, and the formulation may be lyophilized and the lyophilized mixture reconstituted as described above.

As mentioned above, it is preferred not to admix the components, but rather to administer them separately. If the formulation contains two or more of the components, the relative amounts of each may vary within the ranges described above depending on the efficacy obtained.

The IL-2 herein may be any IL-2 prepared from tissue cultures or by recombinant techniques, and from any mammalian source such as, e.g., mouse, rat, rabbit, primate, pig, and human. Preferably the IL-2 is from a human source. More preferably the IL-2 is recombinant.

The recombinant IL-2 may be obtained as described by Taniguchi et al., *Nature,* 302:305-310 (1983) and Devos, *Nucleic Acids Research,* 11:4307-4323 (1983) by cloning the native human IL-2 gene and expressing it in transformed microorganisms. It may also be an IL-2 mutein as described in U.S. Pat. No. 4,518,584, in which the cysteine normally occurring at position 125 of the wild-type or native molecule has been replaced by a neutral amino acid such as serine or alanine, or an IL-2 mutein as described in copending U.S. application Ser. No. 893,186 filed Aug. 5, 1986, now abandoned, the disclosure of which is incorporated herein by reference, in which the methionine normally occurring at position 104 of the wild-type or native molecule has been replaced by a neutral amino acid such as alanine.

In one embodiment, the IL-2 is an unglycosylated protein which is produced by a microorganism which has been transformed with the human cDNA sequence or a modified human cDNA sequence of IL-2 which encodes a protein with an amino acid sequence at least substantially identical to the amino acid sequence of native human IL-2, including the ability to form the disulfide bond between the cysteines at positions 58 and 105, and has biological activities which are common to native human IL-2. The IL-2 may also be produced from yeast or other hosts, as described above. Substantial identity of amino acid sequences means the sequences are identical or differ by one or more amino acid alterations (deletions, additions, substitutions) which do not cause an adverse functional dissimilarity between the synthetic protein and native human IL-2. Examples of IL-2 proteins with such properties include those described by Taniguchi et al., *Nature* (1983), 302:305-310; Devos, *Nucleic Acids Research* (1983), 11:4307-4323; and by European Patent Publication Nos. 91,539 and 88,195; in U.S Pat. No. 4,518,584, supra, and in copending U.S. application Ser. No. 810,656 filed Dec. 17, 1985, supra. Most preferably, the IL-2 is the des-ala$_1$-IL-2$_{ser125}$ mutein in which the N-terminal alanine of the native IL-2 is deleted and the cysteine at position 125 of the native IL-2 is replaced by a serine residue, the des-ala$_1$-IL-2 ala$_{104}$ser$_{125}$ mutein in which the methionine at position 104 of the native IL-2 is replaced by an alanine residue and the cysteine at position 125 is replaced by a serine residue, or IL-2 wherein any combination of up to five of the first five N-terminal amino acid residues are deleted.

The IL-2 may be produced and purified to clinical purity by the method described and claimed in U.S. Pat. No. 4,569,790, issued Feb. 11, 1986, the disclosure of which is incorporated herein by reference.

The antibodies useful herein are produced from hybridomas prepared from antibody-producing fusion partners. Such fusion partners are generated by immunizing mice with live human cancer cells, such as breast cancer cells, or membrane extracts made therefrom. The mice are inoculated intraperitoneally with an immunogenic amount of the cells or extract and then boosted with similar amounts of the immunogen. Spleens are collected from the immunized mice a few days after the final boost and a cell suspension is prepared therefrom for use in the fusion.

Hybridomas are prepared from the splenocytes and a murine tumor partner using the general somatic cell hybridization technique of B. Kohler and C. Milstein, *Nature* (1975) 256:495-497 as modified by Buck, D. W. et al., In Vitro (1982) 18:377-381. Available murine myeloma lines, such as those from the Salk Institute, Cell Distribution Center, San Diego, Calif., USA, may be used in the hybridization. Basically, the technique involves fusing the tumor cells and splenocytes using a fusogen such as polyethylene glycol. After the fusion the cells are separated from the fusion medium and grown in a selective growth medium, such as HAT medium, to eliminate unhybridized parent cells. The hybridomas are expanded, if desired, and supernatants are assayed for anti-human cancer activity by conventional immunoassay procedures (e.g., radioimmunoassay, enzyme immunoassay, or fluorescence immunoassay) using the immunizing agent (cancer cells or membrane extract) as antigen. Positive clones are characterized further to determine whether they meet the criteria of the antibodies herein, i.e., whether they selectively bind to human tumor cells.

Hybridomas that produce such antibodies may be grown in vitro or in vivo using known procedures. The monoclonal antibodies may be isolated from the culture media or body fluids, as the case may be, by conventional immunoglobulin purification procedures such as ammonium sulfate precipitation, gel electrophoresis, dialysis, chromatography, and ultrafiltration, if desired.

The preferred monoclonal antibodies for the immunotoxins herein bind selectively to human breast and/or ovarian cancer cells, and, therefore, such cells are used as immunizing agent in the above described protocol.

The important characteristics of the preferred monoclonal antibodies for the immunotoxins are (1) their immunoglobulin class, (2) their selectivity for human breast and/or ovarian cancer cells, (3) the range of human breast cancer cell lines to which they bind, (4) the range of human breast tumor frozen sections to which they bind, and (5) their ability to form an active immunotoxin.

The selectivity and range of a given preferred antibody for the immunotoxin is determined by testing it against panels of (1) human breast cancer tissues and cells and (2) normal human tissues or cells of breast or other origin. In selecting the preferred class of antibodies, approximately 22,000 growing hybridoma cultures were initially screened against the immunizing breast tumor membranes or cell line, a panel of seven normal tissue membranes, a fibroblast cell line, and a breast tumor frozen section. Clones that reacted with the neoplastic materials, but not with the normal materials, were identified in this initial screen and chosen for isotyping and additional screening for selectivity and range. The additional screening involved: sixteen normal tissue sections, five normal blood cell types, eleven non-breast neoplasm sections, twenty-one breast cancer sections, and fourteen breast cancer cell lines.

For the preferred antibodies for the immunotoxins, the words "specificity" and "normal tissue reactivity" are used interchangeably and are defined as the sum of the number of substructures stained in sixteen normal tissue frozen sections and the number of blood cell types bound, divided by the sum of the total number of substructures bound by any of the monoclonal antibodies in all the tissue on which the monoclonal antibodies were tested and five blood cell types tested.

The term "tumor range" is defined as the number of breast tumor frozen sections stained divided by the number of breast tumor frozen sections tested. The term breast cancer "cell line range" is defined as the number of breast cancer cell lines stained divided by the number of breast cancer cell lines tested. The antibodies of the immunotoxins herein preferably have a normal tissue reactivity equal to or less than 0.09, and a breast tumor binding range of equal to or greater than 0.25 or a breast cancer cell line binding range of equal to or greater than 0.25.

Antibodies of five of the thirty-three deposited hybridomas herein were found to recognize the same 200K dalton antigen. Antibodies of four of the thirty-three bound to a 240K dalton intracellular antigen. Three bound to one or more high molecular weight mucins (HMW) and two bound to transferrin receptors in the form of a 95K dalton antigen. All antigen weights mentioned herein were determined by sodium dodecyl sulfate (SDS) polyacrylamide gel electrophoresis under reducing conditions using procedures known in the art.

The immunotoxins herein may be prepared by conjugating a toxin as described above, such as ricin A chain, to one of the above-described antibodies using the coupling agents defined above. The technique for preparing such immunotoxins is described in EP Publication No. 153,114, published Feb. 8, 1985, the disclosure of which is incorporated herein by reference.

The following examples provide a detailed description of the preparation and characterization of representative monoclonal antibodies for conjugation as well as an immunotoxin for use with IL-2 in accordance with this invention. These examples are not intended to limit the invention in any manner. In the examples, all parts and percentages for solids are given by weight/weight unless otherwise indicated, and all parts and percentages for liquids are given by volume/volume unless otherwise indicated.

EXAMPLE I

Antibody Characterization

Fresh post-surgical human breast cancer tissue and a variety of normal tissues were used to prepare membrane extracts by homogenization and discontinuous sucrose gradient centrifugation. Human breast cancer cell lines were obtained from the Breast Cancer Task Force, from the American Type Culture Collection (ATCC), and from Dr. Jorgen Fogh at Memorial Sloan Kettering. The cells were maintained and passaged as recommended by the Breast Cancer Task Force, the ATCC, and Dr. Fogh. For immunizations, either membrane extract containing 100 μg of protein (Lowry assay) or ten million live breast cancer cells were inoculated intraperitoneally into five-week-old Balb/c mice. The mice were boosted identically twice at monthly intervals. Three days after the last boost, the spleens were removed for cell fusion.

Hybridoma Methods

Somatic cell hybrids were prepared by the method of Buck, D. W., et al, supra, using the murine myeloma line Sp-2/0/Ag14. All hybridoma cell lines were cloned by limiting dilution. Half of the fusions employed splenocytes from mice immunized with breast cancer membrane extracts and half used splenocytes from mice immunized with live breast cancer cell lines. Eighty-three thousand four hundred twenty-four wells were generated from those fusions, of which 22,459 exhibited hybridoma growth.

Screening Methods

Hybridoma supernatant was assayed for reactive antibody in either a solid phase enzyme-linked immunosorbent assay (ELISA) with the immunizing breast cancer membrane extract or an indirect immunofluorescence assay with the immunizing breast cancer cell line. For the solid phase membrane ELISA, 40 μl of 0.1 mg/ml breast cancer membrane protein were placed in polyvinyl chloride (PVC) microtiter wells for 12 hours at 4° C. The extract was aspirated and the wells were washed with phosphate buffered saline (PBS) containing 1% bovine serum albumin (BSA). The wells were then incubated with 45 μl of a 1:10 dilution of hybridoma supernatant. The diluent was medium with 25 mM of a buffer, 10% bovine serum, and 0.1% sodium azide. After 30 minutes at room temperature, the wells were again washed and incubated 45 minutes at 37° C. with a 1:200 dilution of peroxidase conjugated goat anti-mouse IgG. The diluent was PBS. The wells were then washed with PBS and reacted with 200 μl of 1,2-azino-di(3-ethylbenzthiazoline sulphonic acid) in 0.1M sodium citrate buffer pH 4.2 for 30 minutes at room temperature. Optical density was measured at 405 nm on a MicroElisa Reader. For each experiment a positive control, anti-beta 2 microglobulin at 5 μg/ml, was reacted with normal human kidney membrane. This gave an optical density of 1.0±0.1 (standard deviation). The background was 0±0.1 optical density units (O.D.) using medium without mouse monoclonal antibody. Wells that gave a reaction on the breast cancer membrane extract of greater than 0.7 O.D. were saved.

For the indirect immunofluorescence cell line assay 100,000 breast cancer cells of the immunizing cell line were placed overnight with appropriate media in each chamber of a set of eight chambered slides. Similarly, 100,000 fibroblast cells from cell line CC95 were incubated overnight in chambered slide wells. The cells were washed with PBS containing 1% BSA. The wells, both breast cancer and fibroblast, were incubated for 30 minutes at 4° C. with 1:10 dilutions of hybridoma supernatant. The cells were again washed and incubated 30 minutes at 4° C. with a 1:50 dilution of fluorescein isothiocyanate (FITC)-conjugated goat F(ab')$_2$ anti-mouse Ig. The cells were washed three times, fixed in 1.5% formaldehyde in PBS for five minutes, and the chambers removed and rinsed in PBS. The slides were then mounted in a composition containing polyvinyl alcohol, glycerol, buffers and a preservative and examined with a fluorescence microscope. Hybridoma wells showing strong fluorescent binding to the breast cancer cells but no fluorescent binding to fibroblasts were saved. Five thousand one hundred fifty-six hybridoma wells revealed breast cancer reactivity in the initial screen.

Supernatants from the 5156 positive wells were then tested in solid phase ELISA with seven normal tissue membrane extracts (liver, lung, colon, stomach, kidney, tonsil, and spleen). Any well supernatant giving an ELISA O.D. greater than 0.3 was discarded. One thousand one hundred one of the supernatants were found to be unreactive with the normal tissue extracts.

The 1101 hybridoma supernatants were tested on frozen sections of human breast carcinoma tissues. Six micron sections were attached to slides, fixed 10 minutes in acetone at 4° C., dried 10 minutes at room temperature, washed with PBS, blocked with horse serum and incubated 20 minutes at room temperature with 100–200 μl neat hybridoma supernatant. The slides were washed with PBS, and finally incubated 20 minutes at 37° C. with a 1:50 dilution of peroxidase conjugated rabbit anti-mouse Ig, washed again with PBS, and finally incubated 7.5 minutes at 37° C. with 0.5 mg/ml diaminobenzidine in 0.05M Tris buffer pH 7.2 containing 0.01% hydrogen peroxide. The slides were stained with hematoxylin, dehydrated and mounted in a medium containing 35.9% methyl/n-butylmethacrylate copolymer, 7.1% butyl benzyl phthalate, and 0.3% 2,6-ditertbutyl-p-cresol. One hundred twenty-four wells yielded breast cancer selective binding and were cloned.

Purification and Class Determination

Immunoglobulin class and subclass of the monoclonal breast cancer selective antibodies were determined by an immunodot assay essentially the same as that described in McDougal et al., *J. Immunol. Meth.* 63:281–290 (1983). Antibodies were also internally labeled by growing 2–3×10$^6$ hybridoma cells for four hours in methionine-free medium containing 0.2 μCi $^{35}$S methionine. $^{35}$S-labeled antibodies were immunoprecipitated with fixed staphylococcus A cells, or with fixed staphylococcus A cells precoated with rabbit anti-mouse immunoglobulin, and the immunoprecipitates were analyzed by SDS-PAGE to determine antibody light and heavy chain mobility, lack of extra chains, and the ability of each antibody to bind staphylococcal protein A.

The antibodies were expanded in vivo. Balb/c or F1 (C57B/6×Balb/c) mice were primed with 0.5 ml pristane intraperitoneally (ip) and after 10–14 days inoculated with one million log phase hybridoma cells in PBS. Ascites fluid was stored at −70° C. and thawed and filtered through a 0.8 micron filter unit before further purification.

Some IgG antibodies that bound staphylococcal protein A were purified by affinity chromatography on protein A-chromatographic resin containing either agarose, dextran and/or acrylamide with pH step gradient elution. IgG antibodies that did not bind protein A were precipitated by addition of ammonium sulfate to 40% saturation at 0° C. or by binding to DEAE or Affigel ™ (Biorad, Richmond, Calif.). Alternatively, IgG antibodies were purified by chromatography using a Sephacryl S-200 column, followed by DEAE cellulose.

The precipitates were redissolved in PBS, dialysed to 20 mM Tris pH 7.2 and chromatographed on a 1.6×50 cm column of diethylaminoethyl cellulose (DEAE) eluting with a 1.5 liter 0–600 mM NaCl gradient at 4° C. at a flow rate of 1 ml/min. In each case, column fractions were monitored by SDS-PAGE and the purest antibody fractions were pooled, concentrated to 1–3 mg/ml, dialysed to PBS/0.02% NaN$_3$, and stored at 4° C.

IgM antibodies were purified by gel filtration material on a 2.6×40 cm column of Sephacryl S-300 or other gel filtration or resin containing agarose, dextran and/or acrylamide, eluting with PBS/0.01% sodium azide at room temperature at a flow rate of 1 ml/min.

Selectivity Determination

For evaluation of their selectivity for breast cancer, the purified antibodies were tested by immunoperoxidase section staining on sections of sixteen normal tissues, and by immunofluorescent cell sorting on five blood cell types. Immunoperoxidase staining was performed as above except that known dilutions of purified antibodies in PBS in the range of 1–40 μg/ml were used instead of hybridoma supernatants. The pure antibodies were first titrated to find the minimal concentration giving strong immunoperoxidase staining on breast cancer sections and then used at the concentration for the normal tissue tests. Peripheral bood cells (platelets, lymphocytes, red blood cells, granulocytes, and monocytes) were prepared by centrifugation using a medium which separates monocytes from polymorphonuclear leukocytes. The cells were reacted with antibody at the optimal concentration determined above for 30 minutes at 4° C., washed, reacted with a 1:50 dilution of fluorescein isothiocyanateconjugated goat anti-mouse Ig for 30 minutes at 4° C., washed again, and examined in a cell sorter. The wash buffer and diluents were PBS with 1% gelatin and 0.02% sodium azide. The cell sorter was equipped with a 76 micron nozzle and a one watt argon ion laser at 488 nm. An 80 mm confocal lens was used on the optical rail assembly for focusing. Other filters used were a 515 nm interference filter and a 515 nm absorbance filter (for scattered laser light) and a neutral density 1.5 filter for forward angle light scatter. Contour plots of log fluorescein fluorescence versus forward angle light scatter were used for sample analysis. No blood cell types showed detectable binding.

The binding behaviors of the preferred antibodies of the second class herein are reported in Table I below. The following abbreviations are used to denote structures bound by the antibodies: Ac, acini; G, glands; T, tubules; D, ducts; L, lumen; W, sweat glands; E, epithelium; S, sebaceous glands; Gr, granulocytes; Mk, megakaryocytes; M, macrophage; Ly, lymphocytes; Bl, Basal layer; Fe, focal epithelium; A, alveolar lining cells; B, Bowman's capsule; Mu, muscle; and I, islets; H, hair follicles; U, glomeruli; and V, vessels/endothelial.

TABLE I

Normal Tissue Bindings of MABS

| MAB | Pan-creas | Eso-phagus | Lung | Kidney | Colon | Sto-mach | Brain | Tonsil | Liver | Heart | Ovary | Skin | Bone Marrow | Uterus | Bladder | Normal Breast |
|---|---|---|---|---|---|---|---|---|---|---|---|---|---|---|---|---|
| 2G3 | 2Ac | 2E | 1A | 2T | P | 1L | 0 | 1E | 0 | 0 | 0 | 0 | 0 | 2L | 2E | 2E |
| 9C6 | 0 | 2E | 0 | 0 | 0 | 1L | 0 | 1Ly, 2E | 0 | 0 | 0 | 0 | 2Gr | 0 | 0 | 2E |
| 32A1 | 1D | 1E | 1A, M | 1T, U | 0 | 0 | 1My | 0 | 0 | 0 | 0 | 1S, W | 0 | 1Mu | 1E | 0 |
| 33F8 | 0 | 2E | 0 | 1T | 0 | 0 | 0 | 1Ly | 0 | 0 | 0 | 1W | 1Mk | 1L | 0 | 0 |
| 35E10 | 0 | 2E | 1A, 1M | 0 | 0 | 1G | 0 | 1Ly | 0 | 0 | 0 | 2W | 2Gr | 0 | 0 | 0 |
| 41B4 | 0 | 0 | 0 | 0 | 0 | 0 | 0 | 1E | 0 | 0 | 0 | 1W | 0 | 0 | 0 | 1E |
| 87H7 | 1D | 1E | 0 | 0 | 1G | 1G | 0 | 1Ly, E | 2 | 0 | 0 | 2H | 0 | 0 | 0 | 1E |
| 106A10 | 1Ac, D | 1E | 1M | 0 | 0 | 0 | 0 | 2E | 2D | 0 | 0 | 2E, W | 0 | 1G | 2E | 2E |
| 113F1 | 2Ac | 2E | 0 | 0 | 0 | 2G | 0 | 1E | 0 | 0 | 0 | 0 | 0 | 0 | 1E | 0 |
| 120H7 | 0 | 1E | 0 | 1T | 0 | 1L | 0 | 0 | 0 | 0 | 0 | 2S | 0 | 2L | 0 | 0 |
| 140A7 | 1Ac, D | 0 | 0 | 2T, B | 0 | 0 | 1Ly | 2 | 0 | 0 | 2E, 1S | 0 | 0 | 0 | 0 | 0 |
| 200F9 | 1Ac | 1E | 0 | 2L | 0 | 0 | 0 | 0 | 0 | 0 | 0 | 2S | 0 | 0 | 0 | 2E |
| 203E2 | 2Ac | 2E | 2A | 1T | 0 | 0 | 0 | 0 | 0 | 0 | 0 | 2S | 0 | 0 | 0 | 2L |
| 219F3 | 1Ac | 0 | 0 | 0 | 0 | 2L | 0 | 1Ly, E | 0 | 0 | 0 | 2H, W | 1-2Gr | 1G | 0 | 2L |
| 245E7 | 1L | 2E | 1A, M | 2T | 0 | 1G | 0 | 1E | 0 | 0 | 0 | 2S | 0 | 2L | 1E | 2E |
| 254H9 | 2Ac | 2E | 1A | 1T | 0 | 1G | 0 | 0 | 0 | 0 | 0 | 0 | 0 | 0 | 0 | 1E |
| 260F9 | 1Ac | 2E | 0 | 1T | 0 | 0 | 0 | 2E | 2D | 0 | 0 | 2E, 2H | 0 | 1L | 2E | 0 |
| 266B2 | 1Ac, 1D | 2E | 0 | 1T | 0 | 0 | 0 | 2E | 0 | 0 | 0 | 2E, 2W | 0 | 0 | 1E | 0 |
| 317G5 | 1Ac, 1 | 0 | 0 | 2T | 1G | 1G | 0 | 0 | 2D | 0 | 0 | 0 | 0 | 1G | 0 | 0 |
| 369F10 | 0 | 0 | 0 | 0 | 0 | 0 | 0 | 1Ly, 1E | 1, 1D | 0 | 1V | 1S | 0 | 0 | 0 | 0 |
| 387H9 | 1D | 1-2E | 0 | 0 | 0 | 1G | 0 | 0 | 1 | 0 | 0 | 0 | 2 | 1G | 2E | 1 |
| 421E8 | 1Ac | 0 | 0 | 0 | 0 | 1G | 1V | 2Ly, 1Bl | 0 | 0 | 0 | 0 | 2 | 1G | 1E | 0 |
| 451C3 | 0 | 0 | 2M | 0 | 2G | 0 | 0 | 0 | 0 | 0 | 0 | 0 | 2 | 1G | 0 | 0 |
| 452E12 | 0 | 0 | 0 | 0 | 0 | 0 | 0 | 0 | 0 | 0 | 0 | 2S | 0 | 0 | 0 | 2 |
| 452F2 | 0 | 0 | 1M | 1T | 1G | 0 | 0 | 0 | 1D | 0 | 0 | 0 | 0 | 1G | 0 | 0 |
| 454A12 | 0 | 1-2E | 0 | 0 | 0 | 0 | 0 | 1E | 1 | 0 | 0 | 1E, H | 0 | 1G | 1E | 1E |
| 454C11 | 1D | 0 | 0 | 1T | 0 | 0 | 0 | 0 | 0 | 0 | 0 | 1E, H | 0 | 1G | 1E | 1E |
| 457D7 | 0 | 0 | 0 | 1T | 0 | 1G | 0 | 0 | 1D | 0 | 0 | 2S | 0 | 0 | 0 | 2 |
| 520C9 | 0 | 0 | 0 | 1T | 0 | 0 | 0 | 0 | 0 | 0 | 0 | 0 | 0 | 0 | 0 | 0 |
| 650E2 | 1Ac, 1 | 0 | 1-2A | 2T | 2G | 0 | 0 | 0 | 2D | 0 | 0 | 0 | 0 | 2G | 0 | 1 |
| 697B3 | 0 | 0 | 0 | 0 | 0 | 0 | 0 | 0 | 0 | 0 | 0 | 2S | 0 | 2L | 0 | 2L |
| 741F8 | 0 | 0 | 0 | 0 | 0 | 0 | 0 | 1E | 0 | 0 | 0 | 0 | 0 | 0 | 0 | 0 |
| 759E3 | 0 | 0 | 0 | 0 | 0 | 0 | 0 | 1Fe | 0 | 0 | 0 | 0 | 0 | 0 | 0 | 0 |
| 788G6 | 0 | 0 | 0 | 2T | 0 | 0 | 0 | 0 | 0 | 0 | 0 | 0 | 0 | 0 | 0 | 0 |

0 = No binding
1 = Moderate binding
2 = Strong binding

Breast Cancer Cell Binding Range Determination

Antibodies were further evaluated for range of breast cancer cell line recognition by immunofluorescence assays on 14 breast cancer cell lines. Table II below reports the results of these tests for the preferred antibodies herein of the second class.

Non-Breast Cancer Binding of Monoclonal Antibodies

Finally, the antibodies were tested by immunoperoxidase staining on eleven non-breast malignancies. The results for the preferred antibodies herein for the second class are reported in Table III below. The numbers are the same as designated in Table 1.

TABLE II

Breast Cancer Cell Line Binding of MABS

| MAB | MCF7 | BT20 | ZR751 | MDA-MB231 | CAMA1 | ALAB | BT549 | BT474 | T47D | MDA-MB157 | MB330 | MDA-SKBR3 | MDA-BT483 | ZR7530 |
|---|---|---|---|---|---|---|---|---|---|---|---|---|---|---|
| 2G3 | 4 | 3 | 3 | 2 | 4 | 2 | 4 | 2 | 3 | 2 | | 3 | 4 | 3 |
| 9C6 | 3 | 0 | 3 | 0 | 4 | 2 | 0 | 3 | 3 | 0 | 0 | 2 | 0 | 2 |
| 32A1 | 3 | 2 | 2 | 2 | 2 | 2 | 0 | 3 | 3 | 2 | 0 | 2 | 1 | 3 |
| 33F8 | 2 | 3 | 2 | 0 | 2 | 3 | 2 | 2 | 0 | 3 | 2 | 2 | 0 | 1 |
| 35E10 | 1 | 0 | 0 | 0 | 0 | 0 | 0 | 2 | 0 | 0 | 0 | 0 | 0 | 2 |
| 41B4 | 1 | 0 | 0 | 0 | 0 | 0 | 0 | 0 | 1 | 0 | 0 | 0 | 0 | 0 |
| 87H7 | 0 | 0 | 1 | 1 | 0 | 0 | 0 | | 0 | 0 | 0 | 1 | 0 | 0 |
| 106A10 | 3 | 3 | 2 | 2 | 2 | 0 | 0 | 2 | 3 | 2 | 2 | 3 | 2 | 2 |
| 113F1 | 3 | 4 | 2 | 2 | 4 | 0 | 0 | 4 | 3 | 3 | 2 | 4 | 2 | 0 |
| 120H7 | 3 | 2 | 3 | 0 | 3 | 0 | 2 | 0 | 0 | 0 | 0 | 2 | 3 | 2 |
| 140A7 | 3 | 2 | 1 | 0 | 2 | 0 | 1 | 0 | 0 | 0 | 3 | 0 | 2 | 1 |
| 200F9 | 3 | 3 | 2 | 0 | 2 | 2 | 3 | 0 | 3 | 2 | 0 | 0 | 3 | 2 |
| 203E2 | 4 | 4 | 3 | 0 | 4 | 2 | 4 | 2 | 4 | 3 | 0 | 2 | 4 | 3 |
| 219F3 | 3 | 3 | 4 | 0 | 4 | 3 | 2 | 3 | 3 | 4 | 0 | 3 | 2 | 3 |
| 245E7 | 4 | 4 | 4 | 2 | 4 | 2 | 4 | 2 | 4 | 4 | | 3 | 4 | 4 |
| 254H9 | 4 | 4 | 4 | 2 | 4 | 1 | 3 | 2 | 4 | 4 | | 2 | 3 | 3 |
| 260F9 | 3 | 3 | 3 | 2 | 3 | 2 | 0 | 2 | 2 | 2 | ND | 4 | 2 | 3 |
| 266B2 | 3 | 2 | 2 | 2 | 3 | 0 | 0 | | 2 | 2 | | 2 | 2 | 2 |
| 317G5 | 2 | 3 | 3 | 0 | 4 | 3 | 1 | | 3 | 4 | 0 | 3 | 2 | 3 |
| 369F10 | 1 | 0 | 0 | 0 | 2 | 0 | 0 | | 0 | 0 | | 0 | 2 | 0 |
| 387H9 | 3 | 2 | 2 | | 3 | 3 | 0 | | 2 | 2 | | 2 | 2 | 2 |
| 421E8 | 2 | | 2 | | 2 | | 0 | | | | | 0 | 2 | 0 |
| 451C3 | 3 | 2 | 2 | | 2 | 2 | 2 | | 4 | 2 | | 2 | 0 | 2 |
| 452E12 | 0 | 0 | 0 | | 0 | 0 | 0 | | 0 | 0 | | 0 | 0 | 0 |
| 452F2 | 0 | 1 | 2 | | 2 | 2 | 0 | | 1 | 0 | | 3 | 2 | 3 |
| 454A12 | 2 | 2 | 2 | | 2 | 3 | 2 | | 3 | 2 | | 2 | 2 | 2 |
| 454C11 | 2 | 2 | 2 | 2 | 2 | 2 | 1 | | 1 | 0 | | 4 | 2 | 4 |
| 457D7 | 0 | 0 | 0 | | 1 | | 0 | | 0 | 0 | | 0 | 2 | 0 |
| 520C9 | 1 | 0 | 1 | | 2 | | 0 | | 1 | 0 | | 3 | 2 | 2 |
| 650E2 | 3 | 2 | 3 | | 3 | | 0 | | 3 | 3 | | 3 | 2 | 3 |
| 697B3 | 2 | | | | 4 | | 3 | | 4 | 3 | | 0 | 4 | 2 |
| 741F8 | 1 | -- | | | 2 | | 0 | | 2 | 0 | | 4 | 2 | 2 |
| 759E3 | 0 | | | | 2 | | | | 2 | | | 3 | 0 | 4 |
| 788G6 | 2 | | | | 2 | | | | 3 | | | 0 | 3 | 2 |

0 = Negative
1 = Weak
2 = Moderate
3 = Strong
4 = Very strong

TABLE III

Nonbreast Cancer Bindings of MABs

| MAB | Colon | Lung | Prostate | Pancreas | Uterus | Lymphoma | Stomach | Bladder | Esophagus | Melanoma | Ovarian |
|---|---|---|---|---|---|---|---|---|---|---|---|
| 2G3 | 2 | 0 | 2 | 0 | 2 | 0 | 2 | 0 | 0 | 0 | 2 |
| 9C6 | 1 | 0 | 0 | 0 | 2 | 1 | 0 | 0 | 0 | 0 | 1 |
| 32A1 | 0 | 0 | 0 | 2 | 0 | 0 | 1 | 0 | 0 | 0 | 0 |
| 33F8 | 0 | 1 | 0 | 0 | 1 | 0 | 0 | 0 | 0 | 0 | 1 |
| 35E10 | 2 | 2 | 1 | 2 | 0 | 2 | 0 | 0 | 0 | 0 | 0 |
| 41B4 | 0 | 0 | 2 | 0 | 0 | 0 | 0 | 0 | 0 | 0 | 0 |
| 87H7 | 0 | 1 | 2 | 0 | 1 | 0 | 0 | 2 | 1 | 0 | 0 |
| 106A10 | 0 | 1 | 1 | 0 | 1 | 1 | 1 | 0 | 1 | 0 | 0 |
| 113F1 | 0 | 2 | 0 | 2 | 1 | 2 | 2 | 0 | 1 | 0 | 0 |
| 120H7 | 0 | 0 | 2 | 0 | 1 | 1 | 0 | 0 | 0 | 0 | 2 |
| 140A7 | 0 | 0 | 0 | 1 | 2 | 1 | 2 | 1 | 0 | 0 | 0 |
| 200F9 | 0 | 1 | 0 | 0 | 0 | 0 | 0 | 0 | 0 | 0 | 1 |
| 203E2 | | | | | | | | | | | |
| 219F3 | 0 | 0 | 1 | 0 | 1 | 1 | 0 | 0 | 0 | 0 | 1 |
| 245E7 | 0 | 2 | 2 | 2 | 2 | 2 | 0 | 0 | 0 | 0 | 2 |
| 254H9 | | | | | | | | | | | |
| 260F9 | 0 | 0 | 1 | 1 | 1 | 0 | 0 | 0 | 1 | 0 | 2 |
| 266B2 | 0 | 1 | 1 | 1 | 1 | 0 | 1 | 0 | 1 | 0 | 1 |
| 317G5 | 1 | 1 | 0 | 0 | 1 | 0 | 0 | 0 | 0 | 0 | 1 |
| 369F10 | 0 | 1 | 1 | 1 | 0 | 0 | 0 | 0 | 0 | 0 | 2 |
| 387H9 | | | | | | | | | | | |
| 421E8 | 1 | 1 | 1 | 1 | 1 | 0 | 0 | 0 | 1 | 1 | 1 |
| 451C3 | 1 | 1 | 1 | 1 | 2 | 1 | 2 | 1 | 2 | 1 | 1 |
| 452E12 | 0 | 0 | 1 | 0 | 1 | 0 | 0 | 0 | 1 | 0 | 0 |

TABLE III-continued

| | Nonbreast Cancer Bindings of MABs | | | | | | | | | | |
|---|---|---|---|---|---|---|---|---|---|---|---|
| MAB | Colon | Lung | Prostate | Pancreas | Uterus | Lymphoma | Stomach | Bladder | Esophagus | Melanoma | Ovarian |
| 452F2 | 0 | 0 | 0 | 0 | 0 | 0 | 0 | 0 | 0 | 0 | 0 |
| 454A12 | 0 | 0 | 0 | 1 | 2 | 0 | 1 | 1 | 2 | 2 | 1 |
| 454C11 | 0 | 0 | 1 | 1 | 2 | 0 | 0 | 0 | 0 | 0 | 1 |
| 457D7 | 0 | 0 | 1 | 0 | 0 | 0 | 0 | 0 | 0 | 0 | 0 |
| 520C9 | 0 | 1 | 1 | 1 | 1 | 0 | 0 | 0 | 0 | 0 | 0 |
| 650E2 | 2 | 2 | 2 | 2 | 2 | 0 | 0 | 0 | 0 | 0 | 2 |
| 697B3 | 0 | 0 | 0 | 0 | 0 | 0 | 0 | 0 | 0 | 0 | 0 |
| 741F8 | 0 | 0 | 0 | 0 | 0 | 0 | 0 | 0 | 0 | 0 | 0 |
| 759E3 | 0 | 1 | 1 | 1 | 0 | 0 | 0 | 0 | 0 | 0 | 0 |
| 788G6 | 0 | 2 | 0 | 0 | 0 | 0 | 0 | 0 | 0 | 0 | 2 |

The tumor breast cancer range, breast cancer cell binding range, and blood cell binding and selectively characteristics for the monoclonal antibodies according to the invention are summarized in Table IV.

TABLE IV

| | MAB Candidates | | | |
|---|---|---|---|---|
| MAB | Blood Cells | Tumor Range | Cell Range | Selectivity |
| 2G3 | 0 | 1.00 | 1.00 | 0.078 |
| 9C6 | 0 | 0.86 | 0.57 | 0.063 |
| 32A1 | 0 | 0.33 | 0.79 | 0.078 |
| 33F8 | 0 | 0.19 | 0.71 | 0.063 |
| 35E10 | 0 | 0.62 | 0.14 | 0.070 |
| 41B4 | 0 | 0.67 | 0.00 | 0.023 |
| 87H7 | 0 | 0.95 | 0.00 | 0.078 |
| 106A10 | 0 | 0.86 | 0.86 | 0.086 |
| 113F1 | 0 | 0.14 | 0.79 | 0.047 |
| 120H7 | 0 | 0.67 | 0.57 | 0.047 |
| 140A7 | 0 | 0.71 | 0.36 | 0.070 |
| 200F9 | 0 | 0.52 | 0.71 | 0.031 |
| 203E2 | 0 | | 0.86 | 0.055 |
| 219F3 | 0 | 0.86 | 0.86 | 0.086 |
| 245E7 | 0 | 1.00 | 1.00 | 0.070 |
| 254H9 | 0 | | 0.92 | 0.064 |
| 260F9 | 0 | 0.52 | 0.92 | 0.089 |
| 266B2 | 0 | 0.71 | 0.83 | 0.070 |
| 317G5 | 0 | 0.43 | 0.77 | 0.055 |
| 369F10 | 0 | 0.81 | 0.17 | 0.023 |
| 387H9 | 0 | 0.29 | 0.91 | 0.086 |
| 421E8 | 0 | 0.81 | 0.57 | 0.055 |
| 451C3 | 0 | 0.38 | 0.91 | 0.070 |
| 452E12 | 0 | 0.52 | 0.00 | 0.023 |
| 452F2 | 0 | 0.24 | 0.55 | 0.000 |
| 454A12 | 0 | 0.29 | 1.00 | 0.031 |
| 454C11 | 0 | 0.76 | 0.75 | 0.078 |
| 457D7 | 0 | 0.55 | 0.10 | 0.039 |
| 520C9 | 0 | 0.25 | 0.40 | 0.008 |
| 650E2 | 0 | 0.86 | 0.90 | 0.008 |
| 697B3 | 0 | 0.81 | 0.88 | 0.070 |
| 741F8 | 0 | 0.18 | 0.63 | 0.000 |
| 759E3 | 0 | 0.14 | 0.78 | 0.008 |
| 788G6 | 0 | 0.62 | 0.83 | 0.016 |

Antibody Affinity and Antigen Density

Several of the antibodies which may be employed herein were iodinated and tested for binding to MCF-7, CAMA1, SKBR3, or ZR7530 cells. The antibodies were labeled with $^{125}$I using chloramine T to a specific activity of approximately 10 $\mu$Ci/$\mu$g. To determine immunoradiochemical purity, 100,000 cpm of two of the labeled antibodies in 0.5 ml fetal calf serum was serially absorbed with five aliquots of target cells for 15 minutes at 0° C. (generally 4,000,000 cells per aliquot), and the remaining radioactivity in the supernatant after each absorption was determined.

For measurements of association constants, known concentrations of labeled and unlabeled monoclonal antibodies were incubated with target cells in fetal calf serum for 15 minutes in ice. Aliquots of the cell/antibody mix were then counted in a gamma counter or filtered through Microfold filter plates (V & P Scientific) and the filters counted. To account for unbound antibody retained in liquid on the filters, controls containing the same concentrations of antibody, but no cells, were done in parallel. Association constants and antigen copy number per target are calculated from the affinity test results and are reported in Table V below.

TABLE V

| Affinity and Antigen Copy Number of MABs | | | |
|---|---|---|---|
| MAB | n | Ka | Cell Line |
| 2G3 | 3700000 | $9.1 \times 10^6$ | MCF7 |
| 9C6 | | | |
| 32A1 | | | |
| 33F8 | | | |
| 35E10 | | | |
| 41B4 | | | |
| 87H7 | | | |
| 106A10 | | | |
| 113F1 | 2300000 | $1.1 \times 10^9$ | MCF7 |
| 120H7 | 210000 | $6.2 \times 10^6$ | MCF7 |
| 140A7 | | | |
| 200F9 | | | |
| 203E2 | | | |
| 219F3 | | | |
| 245E7 | | | |
| 254H9 | | | |
| 260F9 | 30000 | $6.0 \times 10^7$ | MCF7 |
| 266B2 | 80000 | $2.7 \times 10^8$ | MCF7 |
| 317G5 | 3200000 | $1.6 \times 10^6$ | CAMA1 |
| 369F10 | | | |
| 387H9 | | | |
| 421E8 | | | |
| 451C3 | 400000 | $1.4 \times 10^8$ | MCF7 |
| 452E12 | | | |
| 452F2 | 250000 | $6.8 \times 10^6$ | SKBR3 |
| 454A12 | 470000 | $1.2 \times 10^8$ | MCF7 |
| 454C11 | 390000 | $4.8 \times 10^7$ | ZR7530 |
| 457D7 | | | |
| 520C9 | 500000 | $8.2 \times 10^6$ | SKBR3 |
| 650E2 | | | |
| 697B3 | | | |
| 741F8 | | | |
| 759E3 | | | |
| 788G6 | | | |

Characterization of Antigen Specificity

For identifying the antigens recognized by the monoclonal antibodies, immunoprecipitation of the antigens was carried out according to the following method. Eight mm diameter polystyrene balls (Precision Plastic Ball Co.) were covered with 10% fuming nitric acid in glacial acetic acid and were incubated for three hours in a 50° C. water bath. Following the acid treatment, the balls were rinsed three times with distilled water, covered with 1% sodium dithionite in 0.1M NaOH and incubated three hours in a 50° C. water bath. The balls were again rinsed three times with distilled water, covered with 0.1% 1-ethyl-3-(3-dimethylaminopropyl)-carbodiimide (EDAC), 0.2% suberic acid (suberic acid dissolved in dimethylformamide) and incubated overnight at room temperature. The balls were rinsed three times with distilled water, and marked for identification.

Purified monoclonal antibodies were diluted 0.2 mg/ml in 2-(N-morpholino) ethane sulfonic acid buffer, and the previously treated and marked polystyrene balls were placed in individual tubes and covered with 450 microliters diluted antibody and 50 microliters of fresh 1% EDAC. Tubes were capped and incubated at 25° C. for 24 hours. Following this incubation, the balls were rinsed twice with PBS and were either used fresh or were stored for several days at 4° C. before use.

Freshly labeled target cell extracts were prepared from human breast cancer cell lines labeled with $^{125}$-I by the lactoperoxidase method of Marchalonis, J., "An Enzymic Method for the Trace Iodination of Immunoglobulins and Other Proteins", *Biochem. J.* 113:299–305 (1969), or with 35-S by growth in 35-S methionine. The labeled cells were dissolved in solubilization buffer (1% (v/v) Triton X-100, 150 mM NaCl, 5 mM EDTA, 25 mM Tris-HCl, pH 7.5). Four parts of labeled extract were mixed in a vessel with one part solubilization buffer containing 50 mg/ml bovine serum albumin, to give a final concentration of 10 mg/ml BSA. The balls coated with monoclonal antibody were added to the vessel and were incubated four hours on ice with shaking. Labeled antigen was pipetted from the vessel and the balls were rinsed four times with solubilization buffer. The balls were then removed, placed in individual tubes with 100 microliter Laemmli SDS gel sample buffer, and were incubated three minutes in boiling water. The balls were removed and the samples were run on an SDS gel with appropriate standards.

Immunoprecipitation tests on the antibodies indicated that five of them (454C11, 452F2, 520C9, 741F8, and 759E3) all bind a monomeric protein of about 200 K daltons found in cancerous breast tissue. Two of the five (520C9 and 741F8) are believed to recognize the same epitope on the 200K dalton protein. 454C11 and 759E3 bind a second epitope on the same antigen, and 452F2 binds a third epitope on the same antigen. Four of the antibodies (41B4, 87H7, 452E12, 457D7) bound to a 240K-daltons intracellular antigen. Seven antibodies (2G3, 200F9, 203E2, 245E7, 369F10, 697B3 and 788G6) bound to high molecular weight mucins (HMW). Two antibodies (451C3 and 454A12) bound to transferrin receptors in the form of a 95,000-daltons dalton antigen. Neither 451C3 nor 454A12 blocked binding of transferrin to the receptor. The antigen binding characteristics of the monoclonal antibodies according to the invention are summarized in Table VI.

TABLE VI

| MAB | Antigen |
| --- | --- |
| 2G3 | HMW Mucin |
| 9C6 | 70K |
| 32A1 | |
| 33F8 | 66K |
| 35E10 | 80K |
| 41B4 | 240K |
| 87H7 | 240K |
| 106A10 | 55K a |
| 113F1 | 40, 60, 100, 200K Very Diffuse |
| 120H7 | HMW Mucin |
| 140A7 | Glycolipid (pentasaccharide) |
| 200F9 | HMW Mucin |

TABLE VI-continued

| MAB | Antigen |
| --- | --- |
| 203E2 | HMW Mucin |
| 219F3 | |
| 245E7 | HMW Mucin |
| 254H9 | |
| 260F9 | 55K b |
| 266B2 | 55K b |
| 317G5 | 42K c |
| 369F10 | HMW Mucin |
| 387H9 | 40K |
| 421E8 | |
| 451C3 | Transferrin receptor |
| 452E12 | 240K |
| 452F2 | 200K |
| 454A12 | Transferrin receptor |
| 454C11 | 200K |
| 457D7 | 240K |
| 520C9 | 200K |
| 650E2 | 42K c |
| 697B3 | 200K |
| 759E3 | 200K |
| 788G6 | HMW Mucin | a = Different epitope than that bound by 260F9 and 266B2
b = Different epitope than that bound by 106A10; both 260F9 and 266B2 appear to bind to same epitope
c = Cross block each other Antibody Isotype Antibody isotype was determined as follows: A grid of 5-mm squares was lightly drawn in pencil on the nitrocellulose sheet and 1-ml droplets of antiisotype sera (Litton Bionetics, Kensington, Md., rabbit antisera to mouse κ, λ, α, γ1, γ2a, γ2b, γ3, and μ chains) were applied so that each row of squares received one spot of each heavy and light chain reagent. The sheet was incubated one hour at room temperature in a moist chamber, rinsed quickly in PBS-BSA, containing 1% (w/v), and left overnight in PBS-BSA at 4° C. Strips were cut apart with a scissors and stored at 4° C. in PBS-BSA containing 0.02% sodium azide. Alternatively, strips were air-dried and stored desiccated at 4° C. A series of small tubes was prepared containing 3 ml hybridoma culture supernatant or supernatant diluted with PBSBSA. 1:10 dilutions were generally successful; and some supernatants can be diluted as much as 1:200. A nitrocellulose strip was incubated in each tube for one hour at room temperature. The strips were rinsed three times in PBS-BSA and incubated for one hour at room temperature in diluted rabbit anti-mouse-horseradish peroxidase. The strips were rinsed twice in PBS-BSA and twice in Tris buffer. The strips were placed in Tris buffer containing diaminobenzidine and hydrogen peroxide until sufficient color developed on the anti-isotype spots (usually 3–4 minutes). The antibody isotypes are indicated in Table VII.

TABLE VII

| Isotype of MABs | |
| --- | --- |
| MAB | Isotype |
| 2G3 | G1 |
| 9C6 | M |
| 32A1 | G1 |
| 33F8 | G1 |
| 35E10 | M |
| 41B4 | G1 |
| 87H7 | G1 |
| 106A10 | G1 |
| 113F1 | G3 |
| 120H7 | M |
| 140A7 | M |
| 200F9 | G1 |
| 203E2 | G1 |
| 219F3 | G1 |

TABLE VII-continued

| Isotype of MABs | |
|---|---|
| MAB | Isotype |
| 245E7 | G1 |
| 254H9 | M |
| 260F9 | G1 |
| 266B2 | G1 |
| 317G5 | G1 |
| 369F10 | M |
| 387H9 | G1 |
| 421E8 | G1 |
| 451C3 | G1 |
| 452E12 | G1 |
| 452F2 | G1 |
| 454A12 | G1 |
| 454C11 | G2A |
| 457D7 | G1 |
| 520C9 | G1 |
| 650E2 | G1 |
| 697B3 | G1 |
| 741F8 | G1 |
| 759E3 | G1 |
| 788G6 | G1 |

EXAMPLE II

A. Preparation of Ricin A Chain

A soluble recombinant ricin A which requires no solubilization to be subjected to purification and to display cytotoxicity was prepared in accordance with the procedure described in copending U.S. application Ser. No. 837,583, filed Mar. 7, 1986, the disclosure of which is incorporated herein by reference. Briefly, when the coding sequence for ricin A was placed in direct reading frame with the DNA encoding leader sequence of phoA to form a putative fusion peptide, so that the leader sequence is the N-terminal portion of a leader/ricin A chimera, the ricin A sequences so disposed result in the soluble cytotoxic material.

Expression vectors containing the genes for the precursor proteins contained in pRT3 (ATCC Deposit No. 67,027, deposited Mar. 7, 1986), pRT17 (ATCC Deposit No. 67,026, deposited Mar. 7, 1986), and pRT38 (ATCC Deposit No. 67,025, deposited Mar. 7, 1986) or their mutagenized forms were constructed. Transforming host cells with these expression vectors resulted in solubilization of the precursor protein encoded. The arg-arg modified precursor was cleaved with trypsin; the A and B portions of the precursors were produced as separate proteins, as herein described.

In the phoA expression system, the essential component is the terminated phoA leader sequence upstream of, proximal to, and out of frame with the ricin A encoding sequence, wherein the ricin A encoding sequence is initiated by an ATG codon. The two coding sequences must be, of course, provided with a compatible bacterial promoter, which was the phoA promoter already associated with the leader. Additionally, production was improved in the presence of a positive retroregulator sequence which was the positive retroregulator sequences associated with the crystal protein of *B. thuringiensis,* which are described extensively in European Publication 174,785 published Mar. 19, 1986 and incorporated herein by reference. This was provided on bacterial transport vectors which included replicons and selectable markers.

The vectors were then used to transform a suitable procaryotic host, which was grown under conditions suitable for the particular host chosen, most frequently under conditions whereby the promoter placed in control of the expression system was suppressed. The production of the ricin A was then induced by providing conditions which effect expression under control of the chosen promoter and the production permitted to proceed for sufficient time to effect a desired accumulation of product. The protein product was then isolated by disrupting the cells and the cellular debris was removed. The ricin A produced was then further purified using standard techniques known in the art as applied to freely soluble proteins. However, the efficiency of the extraction and purification was enhanced by treating partially clarified extract with phenyl sepharose. The solubility of the ricin A in the sonicate (once separated from the membrane or other associated materials) was shown by its ability to remain in the supernatant when the sonicate was subjected to centrifugation at high speed, 100,000×g for 30 minutes, to spin down insoluble proteins.

A total of 2 ml of this soluble ricin A (at 9.0 mg/ml) was reduced by adding 2 μl of fresh β-mercaptoethanol (to 0.1%) and incubating at room temperature overnight. The 2 ml of reduced ricin A was applied to a G-25 column (Pharmacia) equilibrated with 0.10M sodium phosphate pH 8.0, followed by 0.5 ml of buffer to make 2.5 ml sample application volume. The next 3.0 ml of eluate (buffer was applied) was collected as desalted ricin A.

B. Conjugation of Ricin A to Antibody

A cell line producing an anti-breast monoclonal antibody designated 520C9, described more fully above, was deposited as Accession No. HB8696 on Jan. 8, 1985 in the American Type Culture Collection (ATCC), Rockville, Md. This antibody was reacted with 5,5'-dithiobis-(2-nitrobenzoic acid) at room temperature and then chilled, and then sufficient 2-iminothiolane (IT) was added to give 2.5 IT molecules per antibody molecule, as described in copending U.S. application Ser. No. 842,476, filed Mar. 21, 1986, the disclosure of which is incorporated herein by reference.

A total of 166 μl of propylene glycol was added to 0.84 ml of the IT-derivatized antibody. The 2.32 ml of ricin A chain described above was added to initiate the conjugation reaction. The mixture was incubated at room temperature for two hours.

The conjugation reaction mixture was applied to a Zorbax-GF-250 sizing (gel filtration) HPLC column using an eluting buffer of 0.15M sodium phosphate, pH 8.0. A total of 78% recovery of the purified immunoconjugate was obtained from the column.

C. IL-2

The recombinant IL-2 employed in this example is des-ala$_1$-IL-2$_{ser125}$. The amino acid sequence of this IL-2 differs from the amino acid sequence of native human IL-2 in that it lacks the initial alanine of the native molecule, and the cysteine at position 125 has been changed to serine. Samples of *E. coli* that produce this IL-2 have been deposited by Cetus Corporation in the American Type Culture Collection, 12301 Parklawn Drive, Rockville, Md., USA on Sept. 26, 1983 under accession number 39,452 and on Mar. 6, 1984 under accession number 39,626 under the provisions of the Budapest Treaty.

The IL-2 was processed and purified as described in the text and FIG. 1 of U.S. Pat. No. 4,604,377 issued Aug. 5, 1986, the disclosure of which is incorporated herein by reference, except that the in vitro disulfide bond formation was carried out using cupric chloride, as described in U.S. Pat. No. 4,572,798 rather than o-iodosobenzoate. When the IL-2 was recovered from the chromatography step(s) it was lyophilized and resuspended in a neutral aqueous buffer. The purity of the recombinant IL-2 after the chromatography step(s) was at least about 95% and the IL-2 contained less than about 0.02 ng/ml endotoxin as determined by the Limulus amebocyte assay.

The purified IL-2 was formulated at a concentration of 0.3 mg/ml with 50 mg/ml mannitol.

D. Model

The target cells employed are murine tumor P388 leukemia cells, obtainable from the American Type Culture Collection, Rockville, Md.

E. Subcutaneous Tumor Injection

The tumor cells are harvested from culture suspensions inoculated subcutaneously (sq) or intraperitoneally (ip) into the appropriate type of mouse.

F. Results

IL-2 alone, the immunotoxin described above alone, and IL-2 with the immunotoxin may be administered intraperitoneally to the mice, beginning one day after tumor implantation (Day 1), with the dose and schedule indicated in Table VIII.

TABLE VIII

| Agent(s) | Dose/kg | Schedule |
|---|---|---|
| PBS | | |
| IL-2 alone | 3.75–7.5 × $10^6$ U/kg | Daily for 14 days- begin at Day 1 post-implant |
| Immunotoxin alone | 100 μg/kg | Daily for 7 days- begin at Day 1 |
| IL-2 and Immunotoxin | 3.75–7.5 × $10^6$ U/kg 100 μg/kg | Daily for 14 days- begin at Day 1 Daily for 7 days- begin at Day 1 |

The maximum tolerated dose of IL-2 was found to be between 50 and 100 KU Df IL-2 given daily to nude mice for 14 days and 150–200 KU of IL-2 given daily to immunocompetent mice for 14 days. The administration of the combination of agents as provided in Table VIII is expected to reduce tumor growth greater than the administration of either agent alone.

In an alternative scheduling to that given in Table VIII, the maximum tolerated dose of IL-2 may be administered alone for one week daily ip or im near the tumor, followed by administering one-half the maximum tolerated dose of IL-2 and the maximum tolerated dose of the immunotoxin, as separate intravenous boluses. The dosage and scheduling must be adjusted to obtain efficacious results. Each type of cancer and immunotoxin will require different dosages and schedules, to be determined by routine experimentation.

EXAMPLE III

An immunotoxin (IMT) was constructed as described in Example II except that an anti-breast monoclonal antibody designated 260F9, described more fully above (deposited as ATCC No. HB-8488)was employed instead of 520C9. The resulting immunotoxin was diluted in saline and 0.01% mouse serum albumin.

The IL-2 employed was the same as that used in Example II. The target cells employed were human breast carcinoma cells from a cell line designated MX-1 obtained from the National Institutes of Health. The tumor cells were implanted sq into nude mice.

The scheduling and dosing were as follows. The immunotoxin was administered every other day for a total of six times intravenously at 3.5 μg/20 g mouse and 7.0 μg/20 g mouse. The IL-2 was administered daily for nine days intraperitoneally at 10 kilounits/dose and 100 kilounits/dose. Both started on day 0 (the seventh day after implantation of the tumor) and had overlapping schedules when administered concomitantly. The results are shown in Table IX below:

TABLE IX

| Group | ΔBW* | Deaths | ΔTW** | % T/C*** |
|---|---|---|---|---|
| IL-2 | | | | |
| 10 Ku | 1.03 | 0/5 | 15.0 | 76 |
| 100 Ku | 1.14 | 1/5 | 9.3 | 47 |
| IMT | | | | |
| 3.5 μg | 0.98 | 0/5 | 9.4 | 47 |
| 7.0 μg | 0.92 | 0/5 | 4.7 | 24 |
| Combination | | | | |
| 10 KuIL-2/3.5 μg IMT | 0.92 | 0/5 | 12.9 | 65 |
| 100 KuIL-2/3.5 μg IMT | 0.95 | 1/5 | 11.3 | 57 |
| 10 KuIL-2/7.0 μg IMT | 0.75 | 2/5 | 3.6 | 18 |
| 100 KuIL-2/7.0 μg IMT | 0.86 | 2/5 | 0.9 | 4 |
| Saline Control | 1.09 | 0/5 | 19.8 | 100 |

*ΔBW is change in body weight as measured by the ratio of mean body weight (in g) at 14 days after treatment to mean body weight (in g) at the start of treatment.
**ΔTW is change in tumor volumes as measured by the ratio of mean tumor volume (in mm$^3$) at 14 days after treatment to mean tumor volume (in mm$^3$) at the start treatement.
***% T/C is the ratio of treated tumor volumes to control tumor volumes. (e.g., % T/C = 40 means there was 60% tumor growth inhibition)

The results indicate tat the combination was approximately additive with respect to its antitumor effects; toxicities were enhanced slightly. Alteration of the dose/route/schedule may alter the efficacy and toxicity results.

The monoclonal antibody-producing hybridomas listed below were deposited with the American Type Culture Collection (ATCC) or Invitro International Inc. (IVI) under the terms of the Budapest Treaty on the International Recognition of the Deposit of Microorganisms for the Purposes of Patent Procedure and the Regulations thereunder (Budapest Treaty). This assures maintenance of the viable culture for 30 years from date of deposit. The hybridomas will be made available by ATCC or IVI under the terms of the Budapest Treaty, and subject to an agreement between the assignee of this application, Cetus Corporation, and ATCC or IVI which assures unrestricted availability upon issuance of the pertinent U.S. patent. Availability of the deposited strains is not to be construed as a license to practice the invention in contravention of the rights granted under the authority of any government in accordance with its patent laws. The assignee has agreed that if the cell lines on deposit should die or be lost or destroyed when cultivated under suitable conditions, they will be promptly replaced on notification with a viable culture of the same cell line.

Each hybridoma designation listed in the left column of Table X corresponds to the monoclonal antibody producing the designated monoclonal antibody.

TABLE X

| Cell Line Designation | IVI Accession Number |
|---|---|
| 9C6 | IVI-10056 |
| 41B4 | IVI-10057 |
| 87H7 | IVI-10059 |
| 106A10 | IVI-10060 |
| 120H7 | IVI-10061 |
| 200F9 | IVI-10062 |
| 254H9 | IVI-10063 |
| 421E8 | IVI-10064 |
| 32A1 | IVI-10066 |
| 35E10 | IVI-10067 |
| 140A7 | IVI-10069 |
| 203E2 | IVI-10070 |

TABLE X-continued

| | |
|---|---|
| 219F3 | IVI-10072 |
| 387H9 | IVI-10073 |
| 452E12 | IVI-10074 |
| 454A12 | IVI-10075 |
| 457D7 | IVI-10076 |
| 697B3 | IVI-10077 |
| 741F8 | IVI-10078 |
| 759E3 | IVI-10079 |
| 788G6 | IVI-10080 |
| 451C3 | IVI-10081 |
| 452F2 | IVI-10082 |
| 650E2 | IVI-10083 |

| Cell Line Designation | ATCC Deposit Date | ATCC Accession Number |
|---|---|---|
| 260F9 | 1/27/84 | HB-8488 |
| 2G3 | 1/27/84 | HB-8491 |
| 33F8 | 1/9/85 | HB-8697 |
| 113F1 | 1/27/84 | HB-8490 |
| 245E7 | 1/27/84 | HB-8489 |
| 266B2 | 1/27/84 | HB-8486 |
| 317G5 | 1/27/84 | HB-8485 |
| 369F10 | 12/13/84 | HB-8682 |
| 454C11 | 1/27/84 | HB-8484 |
| 280D11 | 1/27/84 | HB-8487 |
| 520C9 | 1/8/85 | HB-8696 |
| *260F9-1C9 | 11/7/84 | HB-8662 |

*This clone is a descendent of 260F9 and was found to be a better antibody producer than 260F9.

In summary, the present invention is seen to provide a combination therapy for cancer using an amount of anti-tumor immunotoxin and IL-2 together that is pharmacologically effective.

The foregoing written specification is considered to be sufficient to enable one skilled in the art to practice the invention. The present invention is not to be limited in scope by the cell lines deposited, since the deposited embodiment is intended as a single illustration of one aspect of the invention and any cell lines that are functionally equivalent are within the scope of this invention. The deposit of materials therein does not constitute an admission that the written description herein contained is inadequate to enable the practice of any aspect of the invention, including the best mode thereof, nor are the deposits to be construed as limiting the scope of the claims to the specific illustrations that they represent. Indeed, various modifications of the invention in addition to those shown and described herein will become apparent to those skilled in the art from the foregoing description and fall within the scope of the appended claims.

What is claimed is:

1. A composition comprising a mixture, in pharmacologically effective amounts, of IL-2 from a mammalian species and at least one immunotoxin that binds selectively to cells containing the tumor burden.

2. The composition of claim 1 further comprising a pharmaceutically acceptable carrier medium for the IL-2 and immunotoxin.

3. The composition of claim 1 wherein the IL-2 is human IL-2.

4. The composition of claim 3 wherein the IL-2 is recombinantly produced.

5. The composition of claim 4 wherein the IL-2 is mature human IL-2, des-ala$_1$-IL-2$_{ser125}$, des-ala$_1$-IL-2$_{ala104ser125}$, IL-2$_{ser125}$, IL-2$_{ala104}$, IL-2$_{ala104ser125}$, des-ala$_1$IL-2, or des-ala$_1$IL-2$_{ala104}$.

6. The composition of claim 1 wherein the immunotoxin comprises an antibody that selectively binds to human breast or ovarian cancer cells and is IgG or IgM.

7. The composition of claim 6 wherein the immunotoxin comprises an antibody that does not bind to blood cells, has a breast tumor binding range of at least 0.25, or has a breast cancer cell line binding range of greater than or equal to 0.25, and has a normal tissue reactivity equal to or less than 0.09.

8. The composition of claim 7 wherein the immunotoxin comprises an antibody that is selected from the group consisting of: 260F9, 280D11, 245E7, 520C9, 113F1, 226B2, 454C11, 2G3, 33F8, 317G5, 369F10, 9C6, 35E10, 106A10, 387H9, 421E8, 451C3, 454A12, 650E2, 741F8, 759E3, and antibodies that are functionally equivalent to a member of said group.

9. The composition of claim 8 wherein the immunotoxin comprises an antibody that is selected from the group consisting of 260F9 and 520C9, and antibodies that are functionally equivalent to a member of said group.

10. The composition of claim 1 wherein the immunotoxin comprises a recombinant rich A chain.

* * * * *